(12) United States Patent
Holt et al.

(10) Patent No.: US 7,070,918 B2
(45) Date of Patent: Jul. 4, 2006

(54) METHOD FOR ENHANCEMENT OF SPERM SURVIVAL USING SOLUBLE PERIPHERAL PROTEIN FRACTION OF APM

(76) Inventors: William Vincent Holt, 6 Ivy Close, Eastcote, Pinner, Middlesex (GB) HA5 1PU; Alireza Fazeli, 82 Hallam Grange Rise, Sheffield (GB) S10 4BG; Paul Frederick Watson, 50 New Road, Ware, Herts (GB) SG12 7BY ( * ) Notice: Subject to any disclaimer, the term of this patent is extended or adjusted under 35 U.S.C. 154(b) by 376 days.

(21) Appl. No.: 10/284,438

(22) Filed: Oct. 31, 2002

(65) Prior Publication Data

US 2004/0086843 A1    May 6, 2004

(51) Int. Cl.
  *A01N 1/02*    (2006.01)
(52) U.S. Cl. .......................................... 435/2
(58) Field of Classification Search ..................... 435/2
  See application file for complete search history.

(56) References Cited

FOREIGN PATENT DOCUMENTS

WO    WO98/37182    8/1998

OTHER PUBLICATIONS

Thomas et al, Molecular Reproduction & Development 41, 1995, pp. 468-478, Isolation, Culture, and Characterization of . . . .
Gillan et al, Reprod. Fertil. Dev. 12, 2000, pp. 237-244, The interaction of fresh and frozen-thawed ram spermatozoa with . . . .
Lefebvre et al, Biology of Reproduction 56, 1997, pp. 1198-1204 Bovine Sperm Binding to Oviductal Ephithelium Involves . . . .
Green et al, Reproduction 122, 2001, pp. 305-315, Carbohydrate mediation of boar sperm binding to oviductal ephithelial . . . .
Chian et al, Biology of Reproduction 52, 1995, pp. 156-162, Fertilizing Ability of Bovine Spermatozoa Cocultured with . . . .
Dobrinski et al, Biology of Reproduction 56, 1997, pp. 861-869, Membrane Contract with Oviductal Epithelium Modulates the . . . .
Pollard et al, Biology of Reproduction 44, 1991, pp. 102-107, Fertilizing Capacity of Bovine Sperm May Be Maintained by . . . .
Smith et al, Biology of Reproduction 56, 1997, pp. 83-89, Role of Direct Contact between Spermatozoa and Oviductal . . . .
Fazeli et al, Biology of Reproduction 60, 1999, pp. 879-886, Sperm-Oviduct Interaction: Induction of Capacitation and . . . .
Smith et al, Biology of Reproduction 42, 1990, pp. 450-457, The Viability of Hamster Spermatozoa Stored in the Isthmus . . . .
Elliot et al., "Enhanced boar sperm viability with porcine oviductal apical plasma membranes", Society for the Study of Fertility Annual Conference, University of Cambridge, Jul. 2001 (Poster).
Fazeli et al., "Isthmic Apical Plasma Membrane preparations maintain boar sperm viability in vitro in a does dependent manner", The Society for the Study of Reproduction 33rd Annual Meeting, University of Wisconsin, Madison, WI, Jul. 15-18, 2000 (Poster).
Elliot et al., "Peripheral bound membrane proteins are involved in the maintenance of boar sperm viability by oviductal apical plasma membranes in vitro", American Society for Cell Biology 41st Annual Meeting, Washington, DC Dec. 8-12, 2001; Molecular Biology of the Cell, vol. 12, p. 117a.

*Primary Examiner*—Sandra E. Saucier
(74) *Attorney, Agent, or Firm*—Jacobson Holman PLLC

(57) ABSTRACT

A method of improving and/or prolonging sperm viability which comprises contacting spermatozoa with an isolated, cell-free protein fraction of oviductal apical plasma membrane (APM). This finds use in maintenance of sperm viability to increase the success rate of artificial insemination (AI).

10 Claims, 2 Drawing Sheets

METHOD FOR ENHANCEMENT OF SPERM SURVIVAL USING SOLUBLE PERIPHERAL PROTEIN FRACTION OF APM

BACKGROUND OF THE INVENTION

This invention relates to maintenance of sperm viability to increase the success rate of artificial insemination (AI).

AI is now a fundamental technology for the intensive breeding of domestic animals, in human infertility treatments and in wildlife conservation programmes for the breeding of threatened species. Nevertheless, it has become clear that current semen preservation techniques severely compromise the sperm's survival in the female reproductive tract and hence limit the successful application of the technique.

Sperm survival is particularly compromised when spermatozoa cannot be delivered directly into the uterus because the cervical anatomy is too complex, for example in sheep. This significantly reduces the efficiency of AI. Large numbers of viable spermatozoa must be used to maximize the chance of fertilization, therefore making this technique uneconomical. Surgical intrauterine insemination by laparoscopy is an efficient way of solving this problem and through use of this method conception rates of 80% are now common in sheep and other species. However, this method increasingly is regarded as unacceptable for routine agricultural use on grounds of welfare; routine use of this surgical approach is expected to be curtailed within a relatively short period.

Means to improve the success rate of non-surgical methods is therefore urgently required. One means of achieving this will be by extending the lifespan of spermatozoa in the female reproductive tract.

Following mating (natural insemination), inseminated mammalian spermatozoa are transported to the oviduct where a reservoir of spermatozoa is formed. Studies in several species have shown that the reservoir is limited to the caudal isthmus. The spermatozoa are held in the isthmus until ovulation, when a small number are released to meet the egg(s). During storage in the isthmus, many spermatozoa attach to the oviductal epithelial cells. Attachment to oviductal epithelial cells is important in maintaining sperm viability both in vivo and in vitro. Spermatozoa attachment to oviductal epithelial cells is initiated by uncapacitated spermatozoa. The process of capacitation, along with the switch to the hyperactivated flagellar beating pattern, appears to coincide with the ability of spermatozoa to be released from the oviductal reservoir.

Coculture with whole oviductal epithelial cells in vitro improves the viability of sperm from a number of species including rabbit, cow, sheep, horse, pig and human. It seems this is a widespread characteristic of oviductal cells. However the mechanism by which oviductal cells maintain sperm viability is unknown. Both oviductal secretory products and direct membrane contact between spermatozoa and oviductal epithelial cell membranes have been reported to bestow this beneficial effect.

Many studies in the past have only investigated the role of oviductal secretory products (proteins) on spermatozoa.

Oviductal secretory products have been reported to improve the viability of sperm. These secreted proteins are present in oviduct fluid and the fluids from which they are derived are collected via indwelling cannulae in the ampulla and isthmus of the oviduct. These secreted proteins are not derivable from whole oviductal cells in vitro, but must be collected by cannulation of the oviduct of cycling animals.

Catalase is an example of a secretory protein; this enzyme is known to protect spermatozoa against damage by reactive oxygen species.

The inventors have shown previously that whole oviduct epithelial cells could be isolated and cultured, and that when co-incubated with spermatozoa at 39° C., the life of the spermatozoa could be extended for 2 to 3 days beyond the maximum lifespan of control spermatozoa incubated without cells. Sperm lifespan was judged by the use of tests for plasma membrane integrity.

The inventors have further shown that incubation of spermatozoa with porcine oviductal apical plasma membrane (APM) extends the life of the cultured spermatozoa.

SUMMARY OF THE INVENTION

According to a first aspect of the present invention there is provided a method of improving and/or prolonging sperm viability which comprises contacting spermatozoa with an isolated, cell-free protein fraction of oviductal APM.

By "protein" is meant a protein associated with the apical plasma membrane, but which does not form an integral part of the phospholipid bilayer. An example of such a protein is a peripheral membrane protein; these are associated with membranes but do not penetrate the hydrophobic core of the membrane. They are often found in association with integral membrane proteins and can be removed from membranes by means that do not require the disruption of the membrane structure, for example salt washes.

By "fraction" is meant a part obtainable by precipitation and centrifugation of the APM of oviductal epithelial cells, which contains proteins associated with the apical membrane. This fraction does not include secretory proteins present in oviductal fluid.

By "isolated, cell-free" is meant the fraction is substantially free from any intact cells and other proteins not originating from plasma membrane.

By "improving sperm viability" is meant that the proportion of spermatozoa which are viable is greater in comparison with control spermatozoa.

By "prolonging sperm viability" is meant that the spermatozoa maintain their viability for a longer time period than the normal lifespan of control spermatozoa which is not contacted with the membrane fraction. This longer time period preferably extends for from one day to three days, or greater than three days.

Preferably the spermatozoa are contacted with an isolated, cell-free peripheral membrane protein fraction of oviductal APM in vitro.

In another aspect of the present invention the spermatozoa are boar spermatozoa and the peripheral membrane fraction is of porcine oviductal APM.

According to the present invention there is provided a method of improving and/or prolonging sperm viability following cryopreservation which comprises contacting spermatozoa with an isolated, cell-free peripheral membrane protein fraction of oviductal apical plasma membrane (APM).

According to the present invention there is provided a method of improving and/or prolonging sperm viability during cryopreservation which comprises contacting spermatozoa with an isolated, cell-free peripheral membrane protein fraction of oviductal apical plasma membrane (APM).

According to the present invention there is provided a method of improving and/or prolonging sperm viability during in vitro fertilisation which comprises contacting spermatozoa with an isolated, cell-free membrane protein fraction of oviductal apical plasma membrane (APM).

According to the present invention there is provided a method of isolating a protein having sperm viability improving and/or prolonging activity from oviductal APM comprising the steps of:
(i) harvesting mammalian oviduct epithelial cells;
(ii) separation and isolation of a plasma membrane preparation using a magnesium chloride solution, and centrifugation to obtain a crude APM fraction;
(iii) extraction of a soluble fraction from the crude APM fraction using a salt solution and centrifugation of the solution obtained;
(iv) concentration of the supernatant and washing, to obtain protein.

Preferably the salt solution used in step (iii) above is sodium chloride solution.

According to the present invention there is provided an oviductal APM protein having sperm viability improving and/or prolonging activity, the oviductal APM peripheral membrane protein(s) obtainable according to the following method:
(i) harvesting mammalian oviduct epithelial cells;
(ii) separation and isolation of a plasma membrane preparation using a magnesium chloride solution, and centrifugation to obtain a crude APM fraction;
(iii) extraction of a soluble fraction from the crude APM fraction using a salt solution and centrifugation of the solution obtained;
(iv) concentration of the supernatant and washing, to obtain protein.

Preferably the salt solution used in step (iii) above is sodium chloride solution.

According to the present invention there is provided a method of improving and/or prolonging sperm viability comprising contacting spermatozoa with an isolated, cell-free protein fraction of oviductal apical plasma membrane (APM) in which the spermatozoa are microencapsulated.

By "microencapsulated", is meant that the spermatozoa are enclosed within a semi-permeable membrane. Examples of membranes which can be used include beeswax, starch, gelatine, and polyacrylic acid and polylysine.

Preferably, the treated spermatozoa are microencapsulated in a semi-permeable membrane comprising polylysine.

According to the present invention there is provided a method for improving and/or prolonging sperm viability which comprises contacting spermatozoa with an isolated, cell-free peripheral membrane protein fraction of oviductal apical plasma membrane (APM) in which the protein is linked to an inert polymer.

Preferably, hydrophilic polymers are used; these are defined as polymers having a solubility of greater than 10 g/L in an aqueous solution, at a temperature between 0 to 50° C. The aqueous solution can include small amounts of water-soluble organic solvents, such as dimethylsulfoxide, dimethylformamide, alcohols or acetone. Examples of polymers which may be used in the present invention include synthetic polymers such as polyethylene glycol, polyvinyl alcohol, polyvinylpyrrolidone, hydroxylated celluloses, polypeptides, polysaccharides such as polysucrose or dextran and alginate. An example of a polymer which may be used in the present invention is amine and carbonyl-reactive dextran.

By "linked" it is meant that the polymers are joined to the proteins; the join may be through an ionic or covalent bond.

Linking proteins to inert polymers can result in the advantages of increased efficiency and reduced toxicity.

According to the present invention there is provided a method for improving and/or prolonging sperm viability which comprises contacting spermatozoa with an isolated, cell-free peripheral membrane protein fraction of oviductal apical plasma membrane (APM) in which the peripheral membrane protein fraction(s) of oviductal APM or component(s) obtainable therefrom is at a concentration of between approximately 0.1 µg/L and approximately 1 g/L.

Preferably a concentration of between approximately 5 µg/L and approximately 400 µg/L is used. More preferably the concentration used is between approximately 25 µg/L and approximately 200 µg/L.

According to the present invention there is provided a method of improving and/or prolonging semen survival following sex-sorting of the spermatozoa for X- (female) and Y-bearing (male) spermatozoa cells which comprises contacting spermatozoa with an isolated, cell-free protein fraction of oviductal apical plasma membrane (APM).

According to the present invention there is provided an isolated, cell-free protein fraction of oviductal apical plasma membrane (APM), having sperm viability improving and/or prolonging activity.

According to the present invention there is provided a sperm diluent which includes an additive comprising an isolated, cell-free peripheral membrane protein fraction of oviductal apical plasma membrane (APM) having sperm viability improving and/or prolonging activity.

Preferably, the sperm diluent or additive is synthetic. By synthetic we mean the diluent or additive is synthesised de novo. The advantage of synthetic diluents or additives is that these substantially eliminate the risk of transmitting viruses or other contaminants which might be associated with products obtained directly from mammalian tissue.

According to the present invention there is provided a use of an isolated, cell-free peripheral membrane protein fraction of oviductal apical plasma membrane (APM), in the manufacture of a composition for improving and/or prolonging sperm viability following cryopreservation.

According to the present invention there is provided a use of an isolated, cell-free peripheral membrane protein fraction of oviductal apical plasma membrane (APM), in the manufacture of a composition for improving and/or prolonging sperm viability during cryopreservation.

According to the present invention there is provided spermatozoa together with an isolated, cell-free peripheral membrane protein fraction of oviductal APM having sperm viability improving and/or prolonging activity, which are microencapsulated with a semi-permeable membrane.

BRIEF DESCRIPTION OF THE DRAWINGS

The invention will next be described in more detail by way of example with reference to the accompanying drawings in which.

DETAILED DESCRIPTION OF THE PREFERRED EMBODIMENTS

Oviduct and Lung Tissue Preparation

Figure 1:
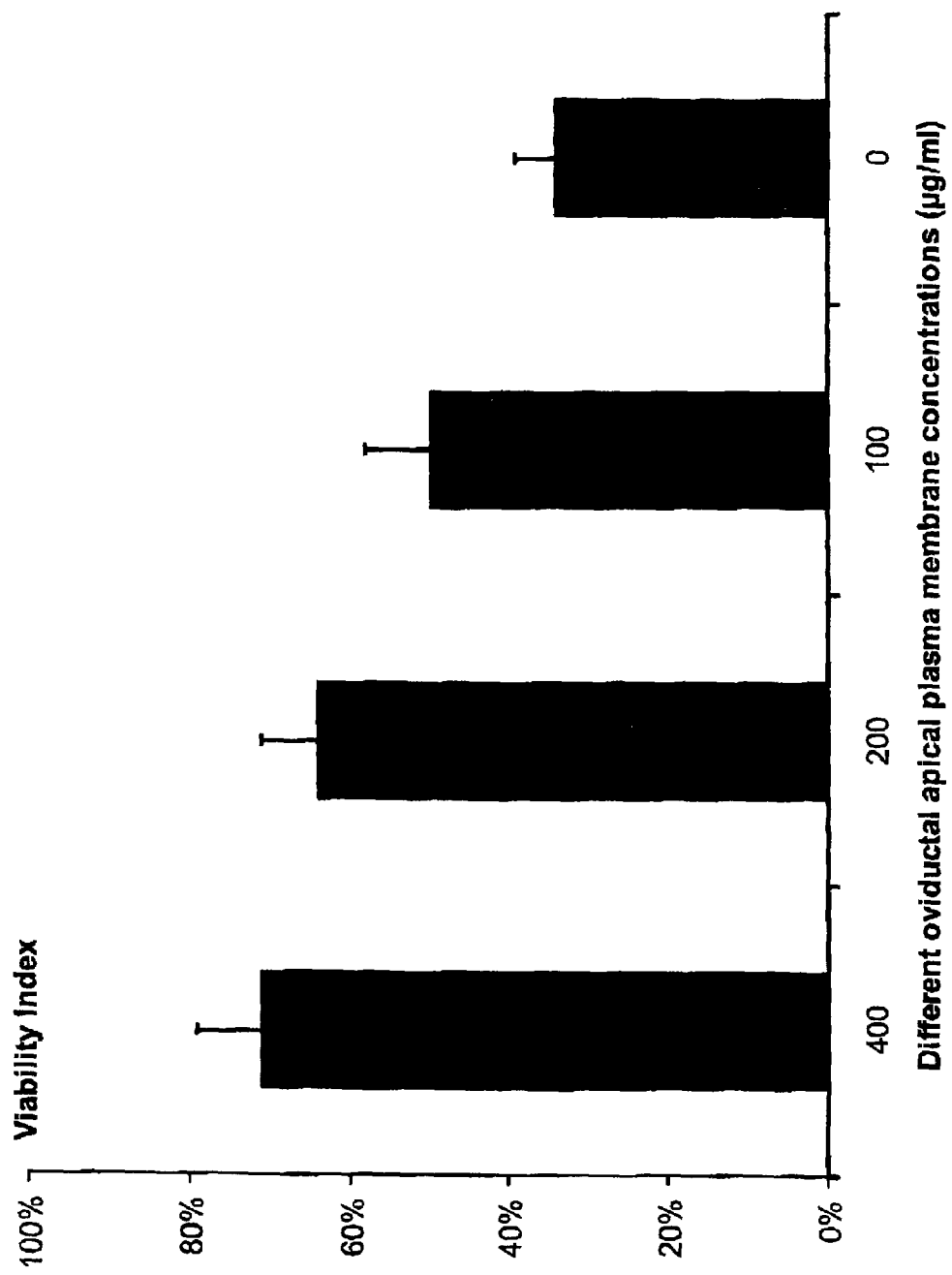
FIG. 1 shows the viability index (Mean±SEM) of boar spermatozoa incubated with different concentrations of oviductal APM preparations.

Porcine lung and oviduct tissues were obtained and oviducts (attached to ovaries) were cleaned and washed with cold PBS. The oviducts were divided into two groups designated: FOL (follicular) and LUT (luteal), based on the appearance of the associated ovaries. Those oviducts attached to ovaries containing large follicles (8–12 mm in diameter) with signs of recent ovulation and no corpora lutea were assigned to the FOL group, those with ovaries containing several corpora lutea, without large follicles were assigned to the LUT group. Oviducts in both groups were trimmed from the ovaries and washed by passing four times through PBS. Each oviduct was divided into three sections; the first, designated as ampulla, was a section between the fimbria and the middle (thicker part) of the oviductal tube. The second section designated as isthmus, consisted of 1–2 cm of the caudal part of the uterine horn, the uterotubal junction, and up to nearly the middle (thinner part) of the oviductal tube. Finally, a section around the junction of the thin and thick part of the oviductal tube, approximately 2–3 cm long, was excised and discarded to assure differentiation of isthmic and ampullar parts of the oviduct. Each oviduct section (isthmic or ampullar) was processed separately. They were opened longitudinally and epithelia were scraped into a petri dish using a clean glass microscope slide. Scraped tissues collected from approximately 8–12 oviduct sections were collected separately (FOL isthmus, FOL ampulla, LUT isthmus and LUT ampulla) into 20 ml of cold PBS and kept on ice. These suspensions were centrifuged for five minutes at 200 g. The supernatants were discarded and pellets were resuspended in 20 ml of buffer 1 containing 60 mM mannitol, 5 mM EGTA, 1 µM phenylmethylsulfonylfluoride (PMSF), Tris base (pH 7.4). Suspensions (5 ml) were snap frozen in liquid nitrogen and stored at −80° C. until subsequent use for APM preparation.

Porcine lung tissues were chopped finely to a volume of 5 ml to which 20 ml of Buffer 1 was added. The lung tissue homogenates were snap frozen in liquid nitrogen and stored at −80° C. until subsequent use for APM preparation.

Porcine duodenal tissues (8–12 cm) were opened longitudinally and epithelia were scraped into a petri dish using a clean glass microscope slide. Scraped tissues were collected into 20 ml of cold PBS and kept on ice. These suspensions were centrifuged for five minutes at 200 g. The supernatants were discarded and pellets were resuspended in 20 ml of buffer 1 (pH 7.4). Suspensions (5 ml) were snap frozen in liquid nitrogen and stored at −80° C. until subsequent use for APM preparation.

APM Preparation

Tissue homogenates were thawed and homogenized on ice for one minute using a small homogeniser (Silverson, Waterside, UK). Two hundred microliter aliquots of this initial homogenate were snap-frozen in liquid nitrogen and stored at −80° C. for subsequent analysis. The homogenate was supplemented with 200 µl of 1 M $MgCl_2$ followed by 30 minutes incubation on ice. Thereafter the homogenate was centrifuged for 15 minutes at 3000 g. The pellet was discarded and the supernatant was centrifuged for 30 minutes at 90,000 g. After centrifugation, the pellet was resuspended in 20 ml of buffer 2 containing 60 mM mannitol, 7 mM EGTA, Tris base (pH 7.4) with ten strokes of a Potter S homogenizer. The homogenate was supplemented with 200 µl 1 M $MgCl_2$ and incubated on ice for 30 minutes. Afterwards, the mixture was centrifuged at 3000 g for 15 minutes. The pellet was discarded and the supernatant was centrifuged at 90,000 g for 30 minutes. The pellet, following ultracentrifugation, was resuspended in 20 ml of a modified Tyrode's medium containing 2 mM $CaCl_2$, 3.1 mM KCl, 0.4 mM $MgCl_2 6H_2O$, 100 mM NaCl, 25 mM $NaHCO_3$, 0.3 mM $NaH_2PO_4 2H_2O$, 10 mM HEPES, 21.6 mM Sodium lactate and 1 mM sodium pyruvate with ten strokes of a Potter S homogenizer. The suspension was centrifuged for 30 minutes at 90,000 g. The supernatant was discarded and the pellet was resuspended in 900 µl of the modified Tyrode's medium by aspiration through a 0.9×90 mm Yale spinal needle (Becton Dickinson, Oxford, UK). This fraction was portioned, snap-frozen in liquid nitrogen and stored at −80° C.

Protein and γ-glutamyl Transpeptidase Activity Analysis

Protein concentrations of initial homogenates, final APM preparations from different tissues, and peripheral membrane protein fractions obtained from oviductal APM, were measured (Bio-Rad Protein Assay kit, Bio-Rad, Hemel Hempstead, UK). The kit is based on a dye-binding assay, in which the colour of the dye changes differentially, in response to change in protein concentration.

γ-glutamyl transpeptidase has previously been shown to reside mainly in the APM of polarized epithelial cells. The activity of γ-glutamyl transpeptidase in the initial homogenate and in the APM preparations was measured calorimetrically, using the Sigma diagnostic kit 545 (Sigma, Poole, Dorset, UK). The assay is based on the transfer of the glutamyl group from L-glutamyl-p-nitroanilide to glycylglycine catalyzed by γ-glutamyl transpeptidase. The liberated p-nitroaniline is diazotized by the addition of Sodium Nitrite and Ammonium Sulfamate. The absorbance of the pink azo-dye resulting from the addition of N-(1-napthyl)-ethylenediamine, measured at 530–550 nm, is proportional to γ-glutamyl transpeptidase activity. The degree of enzyme enrichment was expressed as fold increase in γ-glutamyl transpeptidase activity in the final APM preparations compared to the initial homogenate. This demonstrated the success of the method employed to isolate APM preparations from the initial homogenates. In addition, distinct differences in the protein profile of APM preparations were observed compared to that of original homogenates. Three proteins diminished and three were enriched in APM preparations compared to that of the initial oviductal homogenates.

Gel Electrophoresis

Protein separation was performed using the discontinuous buffer system. Five µg protein of original homogenate and purified APM preparations obtained from FOL isthmic, FOL ampullar, LUT isthmic, LUT ampullar and lung tissues were loaded on SDS-polyacrylamide gels (12% separation, 5% stacking). Gels were electrophoresed for between approximately 45 mins to 1 hr at between approximately 180 to 200 volts. Gel electrophoresis procedures were carried out using a Bio-Rad Modular Mini Electrophoresis System (Bio-Rad Labs, Hemel Hempstead, Herts, UK). Following electrophoresis the gels were fixed and then stained with Brilliant Blue G-Colloidal concentrate (Sigma). A digital image was produced from stained gels using a Hewlett Packard Scanjet 6200c scanner (CA, USA). The image was further analyzed using Scion Image Beta 4.0.2 software program (Scion Corporation, Maryland, USA). Protein profiles of oviduct peripheral membrane proteins, pellet left after the recovery of peripheral membrane proteins and oviductal APM were produced and analyzed using the methodology described above.

Semen Preparation

Boar semen, diluted and stored for 24 hrs in Beltsville thawing solution was obtained and the semen (45 ml) washed three times with PBS by centrifugation and resuspension (600 g for 10 min). After the last centrifugation the supernatant was discarded, and the pellet was resuspended in the modified Tyrode's medium supplemented with 12 mg/ml BSA, 200 U/ml penicillin, 200 μg/ml streptomycin and 0.5 μg/ml amphotericin B (Life Technologies, Paisley, UK) (supplemented Tyrode's medium). One ml of washed semen sample was overlaid with 500 μl of supplemented Tyrode's medium. The tube was placed at a 45° angle in an incubator held at 39° C. in a humidified atmosphere saturated with 5% $CO_2$. After one hour the top 0.5 ml of medium containing the swim-up spermatozoa fraction was collected. Spermatozoa concentration was measured using a counting chamber. Sperm viability was assessed using a combination of Ethidium homodimer-1(ETHD-1; Molecular Probes, Leiden, The Netherlands) and SYBR-14 (Molecular Probes). One μl of 2 mM ETHD-1 and 2.5 μl of 20 pM SYBR-14 were diluted in 1 ml of PBS. An equal volume of the dye mixture was added to the semen sample and incubated for 20 minutes at 39° C. An aliquot of this preparation was placed on a slide and evaluated by epifluorescence microscopy (×40 objective). Viable spermatozoa with intact membrane excluding ETHD-1 demonstrated green fluorescence over the nucleus due to SYBR-14 staining. Spermatozoa with disrupted membranes showed red nuclear fluorescence due to ETHD-1 staining. Two hundred spermatozoa were evaluated by fluorescence microscopy and classified as membrane intact (green) or membrane damaged (red).

Sperm-APM Coincubation

Swim-up spermatozoa fractions ($50 \times 10^6$ spermatozoa/ml) in 25 μl aliquots were added to 25 μl of APM (variable concentrations depending on experimental design). Sperm-APM coincubation droplets were covered with mineral oil, incubated at 39° C., 5% $CO_2$ for 24 hrs. After coincubation 50 μl of PBS containing 20 μM SYBR-14 and 2 μM ETHD-1 was added to each droplet and further incubated for 15 min. Thereafter the sperm viability was assessed as described above.

Microencapsulation of Sperm

Suspensions of sperm in physiological saline containing 1% sodium alginate (w/v), pH 6.8, were passed through a syringe pump to form droplets having a mean diameter of between 0.75 and 1.5 mm. Briefly, the sperm suspension within a 10 ml syringe was forced through a 19 gauge hypodermic needle contained within an encapsulating jet at a rate of approximately 1.5 ml/min to form droplets which were collected in a beaker containing aqueous solution (80 ml) of 1.5% $CaCl_2$-Hepes buffer (50 mM) pH 6.8. Immediately on contact with the $CaCl_2$-Hepes buffer solution, the droplets absorb calcium ions, which causes solidification of the entire-cell suspension resulting in a shape-retaining, high viscosity microcapsule. To form a semi-permeable membrane on the surface of the microcapsules, the microcapsules were rinsed three times with physiological saline and suspended in physiological saline containing 0.4% polylysine having a molecular weight range of 25 to 50 kDa, the excess polylysine was aspirated and the microcapsules rinsed with 0.1% CHES buffer, pH 8.2. After three rinses with physiological saline, the alginate gel inside the microcapsules was liquefied by suspending the capsules in isotonic 3% sodium-citrate saline solution, pH 7.4 for approximately 5 minutes.

Cryopreservation of Sperm.

Collected semen was allowed to cool slowly to room temperature over a period of around 2 hours. Semen was aliquoted into tubes containing approximately $6 \times 10^9$ spermatozoa and centrifuged at room temperature for 10 minutes at 300 g. The supernatant was removed by aspiration and the spermatozoa resuspended into Beltsville F5 extender (5 ml).

The tubes containing the extended spermatozoa were then placed in a beaker containing water (50 ml) at room temperature, which was then placed into a refrigerator and cooled to 5° C. over a two hour period. After the spermatozoa were cooled, 5 ml of Beltsville F5 extender containing 2% glycerol was added to each tube. The contents of the tubes were mixed by immersion and frozen immediately into pellets of 0.15 ml to 0.2 ml on dry ice. The pellets were then transferred to liquid nitrogen for storage.

When required for insemination, 10 ml of pellets were removed from the liquid nitrogen and held at room temperature for 3 minutes before being placed in a 250 ml beaker containing 25 ml Beltsville thawing solution which had been pre-warmed to 50° C. to thaw the semen.

Preparation of Fertilized Oocytes for IVF Treatment

Ovaries were collected and placed in 0.9 wt % saline containing at 25 to 30° C. Oocytes were aspirated from follicles using a 20 gauge needle connected to a 10 ml disposable syringe, transferred to a 50 ml conical tube and allowed to sediment at room temperature. Supernatant was discarded and follicular contents washed with Tyrode's Lactate (TL)-Hepes medium supplemented with 0.01% PVA (TL-Hepes-PVA). Oocytes with an evenly granulated cytoplasm and surrounded by compact cumulous cells were washed twice with TL-Hepes-PVA and three times in IVM medium. Oocytes were suspended in 500 μl of IVM medium in a four well multidish and cultured for 42 to 44 hours.

On completion of IVM, cumulus cells were removed by treatment with 0.1% (w/v) hyaluronidase in basic IVM medium and vortexed for 1 minute. Denuded oocytes were washed three times in 500 μl of IVM medium and then washed three times in IVF medium containing 1 mM caffeine and 1 mg/ml BSA. Oocytes were placed into 50 μl drops of pre-equilibrated IVF medium and covered with warm paraffin oil in a $35 \times 10$ mm$^2$ polystyrene culture dish. A frozen semen pellet was thawed and washed three times by centrifugation (1900×g for 4 minutes) in Dulbecco's PBS supplemented with 1 mg/ml BSA, 75 μg/ml potassium penicillin G and 50 μg/ml streptomycin sulfate (pH 7.2) The sperm pellet was then resuspended in IVF medium containing 1 mM caffeine and 0.1% (w/v) BSA and 50 μl of the sperm suspension was added to 50 μl drops of IVF medium containing the oocytes. The final sperm concentration was 2.5 to $3.5 \times 10^5$/ml. Spermatozoa and oocytes were incubated for 6 hours at 39° C., 5% $CO_2$ (w/v) in air.

Statistical Analysis

The data were expressed as mean viability index±SEM. Viability index was defined as percentage of viable spermatozoa after 24 hours incubation in comparison to that of the initial viability of the same semen sample at the beginning of incubation period. Sperm viability data were tested for normal distribution. Analysis of variance was used for the statistical analysis of the data. The level of significance was considered $p=0.05$.

The invention will now be further illustrated by means of the following examples.

EXAMPLE 1

Recovery of APM

APM was obtained from isthmic, ampullar, lung and duodenum preparations. The amount of APM recovered from different tissues after each isolation procedure varied on different days (0.65 to 1.1, 1.47 to 4.3, 1.1 and 4.4 mg protein/ml for isthmic, ampullar, lung and duodenum APM preparations, respectively). The γ-glutamyl transpeptidase activity showed an overall increase in APM preparations compared to that of the initial homogenate (5- to 16-fold for isthmic, 5- to 7-fold for ampullar, 7-fold for lung and 3 fold for duodenum).

EXAMPLE 2

Determination of the dose response effect of FOL isthmic APM preparations on the maintenance of boar sperm viability in vitro.

To investigate whether the maintenance of boar sperm viability by APM preparations follows a dose-dependent response, spermatozoa were incubated in the presence of 0 (control), 100, 200 and 400 µg/ml of FOL isthmic APM preparations. Spermatozoa from 6 different boars were used in the experiments.

The overall viability of sperm after swim-up and at the start of coincubation was 68%±3 (mean±SEM). Generally, after swim-up procedures most recovered samples showed different degrees of head to head agglutination.

Agglutination was particularly apparent after incubation in the presence of oviductal APM preparations. This (head to head agglutination) was not induced in samples incubated in the presence of lung APM or control.

The viability index of boar spermatozoa incubated in the presence of FOL isthmic APM preparations was higher than that of the control after 24 hr incubation (FIG. 1). There was a significant concentration effect on the longevity of boar spermatozoa (p<0.01). 100 µg/ml APM increased sperm viability by about 10% over that of control, but viability was almost doubled by incubating 400 µg/ml APM.

EXAMPLE 3

Determination of the specificity of the effect of FOL isthmic APM preparations on the longevity of boar spermatozoa in vitro.

To investigate the specificity of the effect of APM preparations obtained from reproductive tissue in comparison to that of non-reproductive tissue on the maintenance of boar sperm viability, spermatozoa were co-incubated with FOL isthmic APM preparations (200 µg/ml), lung APM preparations (200 µg/ml) and control. Spermatozoa from 6 different boars were used in the experiments.

The viability index of boar spermatozoa incubated for 24 hours in supplemented Tyrode's medium (control) was significantly (p=0.005) lower than that incubated with FOL isthmic APM preparations (31%±9 and 60%±11; respectively). However the viability index of spermatozoa incubated with lung APM preparations (39%±7) was not different from that of the control and it was significantly (p=0.05) lower than that incubated with FOL isthmic APM preparations.

EXAMPLE 4

The effect of oviductal APM origin on the maintenance of boar sperm viability: comparison between FOL phase isthmic and ampullar APM preparations.

To investigate whether the sperm viability maintenance effects of APM depend on the region of oviduct from which APM is obtained, a comparison was made between FOL phase isthmic and FOL phase ampullar APM preparations. Spermatozoa were incubated with FOL phase isthmic APM preparations (200 µg/ml), FOL phase ampullar preparations (200 µg/ml) and control (medium only). Spermatozoa from 6 different boars were used in experiments.

There was no significant difference between the viability index of spermatozoa co-incubated with APM preparations obtained from FOL phase isthmic or FOL phase ampullar tissues (76%±5 and 74%±16; respectively). However there was a significant decrease in the viability of sperm in control (39%±6) compared to that incubated with either of oviductal APM preparations (p=0.001).

EXAMPLE 5

The effect of oviductal APM cycle stage on the maintenance of boar sperm viability: comparison of the effect of FOL and LUT phase oviductal APM preparations on the maintenance of boar sperm viability.

To investigate whether the maintenance of sperm viability effect by oviductal APM depends on the oestrous cycle stage of the sows from which oviductal APM is obtained, a comparison was made between oviductal APM preparations obtained from sows in FOL and LUT stages of the oestrous cycle. Since in the previous experiment no difference was seen between isthmic and ampullar preparations, equal amounts of FOL isthmic and FOL ampullar APM preparations were mixed to provide a FOL oviductal APM preparation. In the case of LUT APM preparation, this was achieved by mixing equal amounts of LUT isthmic and LUT ampullar APM preparations. Spermatozoa were incubated with FOL oviductal APM preparations at 200 µg/ml, LUT oviductal APM preparations at 200 µg/ml and control (medium only). Spermatozoa from 8 different boars were used in these experiments.

Both oviductal APM preparations obtained from sows in the FOL and LUT stages of the reproductive cycle maintained boar sperm viability in vitro to the same extent (82±6 and 84±6; respectively). The viability of sperm co-incubated with these preparations was significantly (p=0.0001) higher than the control (49±9) at the end of the coincubation period (24 hr).

EXAMPLE 6

The effect of heat treatment on the ability of APM preparations to maintain boar sperm viability in vitro.

The oviductal APM preparations were heat treated to investigate whether the maintenance of sperm viability by oviductal APM preparations would be altered. Since in the previous experiment no difference was seen between FOL and LUT phase oviductal preparations, a mixture of both preparations was used in the following experiments. An aliquot of oviductal APM was incubated at 100° C. for 20 minutes. Spermatozoa were incubated with heat-treated oviductal APM preparations at 200 µg/ml, standard oviductal APM preparations at 200 µg/ml and control (medium only). Spermatozoa from 8 different boars were used in experiments.

The non-heated APM (78+/−9) showed significantly (P<0.04) increased viability-enhancing effect than that of the heat treated APM (59+/−5) and the control (65+/−5).

EXAMPLE 7

Determination of the effect of oviductal peripheral membrane protein fraction on the maintenance of boar sperm viability.

To investigate whether peripheral oviductal membrane proteins can maintain the viability of boar spermatozoa in vitro, spermatozoa were co-incubated with aliquots of peripheral membrane proteins (200 μg/ml), aliquots of pellet left after the recovery of peripheral membrane proteins (200 μg/ml), oviductal APM preparations (200 μg/ml), lung APM preparations (200 μg/ml), duodenum APM preparations (200 μg/ml) and control (medium only). Spermatozoa from 12 different boars were used in experiments.

Figure 2:
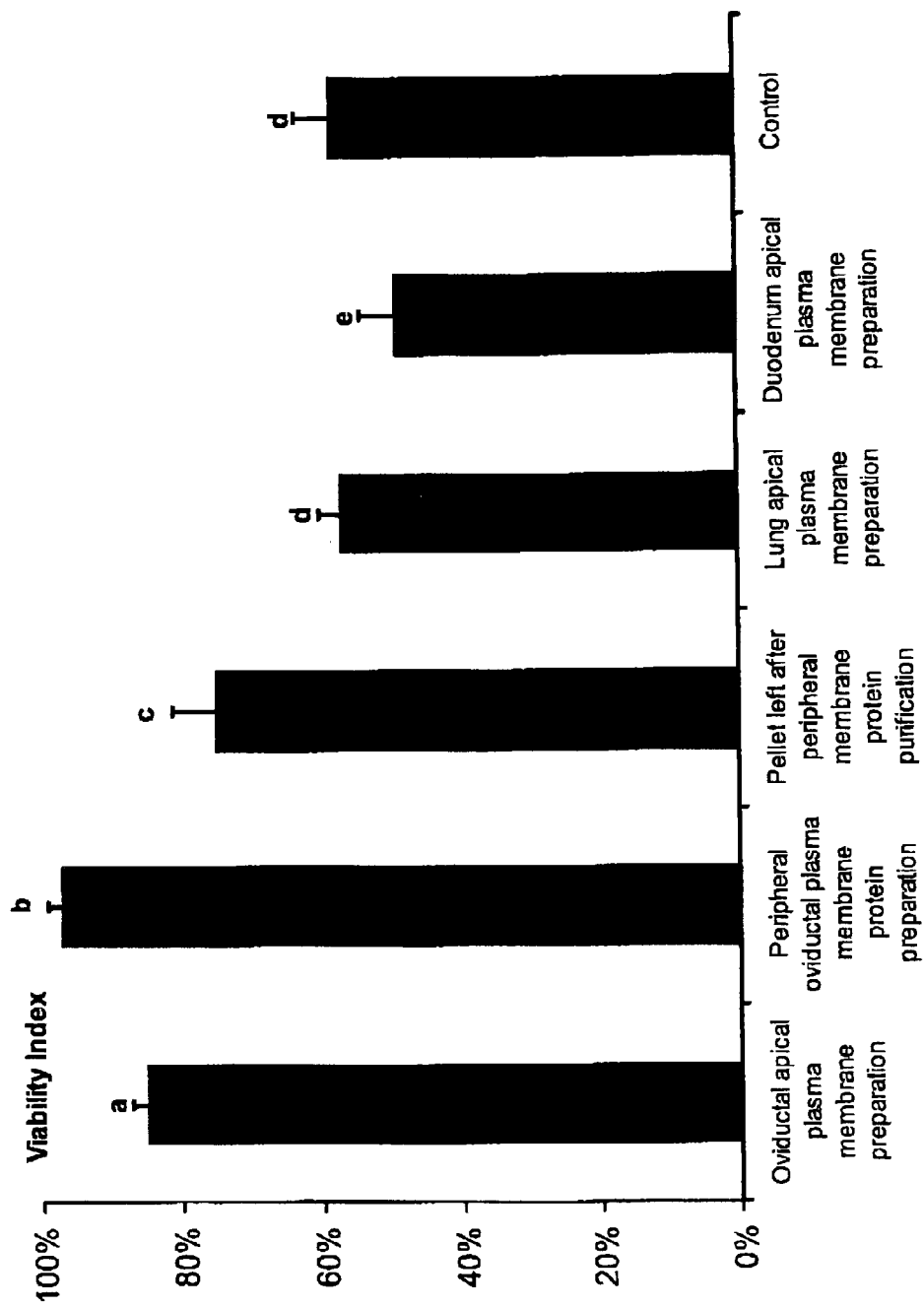
FIG. 2 shows the viability index (Mean±SEM) of boar spermatozoa incubated for 24 hrs with peripheral oviductal APM proteins, pellet left after recovery of peripheral membrane proteins, oviductal APM preparation, lung APM preparation, duodenum APM preparation and control (medium only).

The viability indices of spermatozoa co-incubated with peripheral membrane proteins, pellet left after peripheral membrane proteins recovery and oviductal APM were all significantly (p<0.05) higher than that incubated with lung, duodenum or control (medium only) (FIG. 2). The capacity of peripheral membrane proteins in maintaining sperm viability was significantly higher than that of pellet left after peripheral membrane proteins recovery (p<0.0001) and oviductal APM (p<0.004). The capacity of the pellet left after peripheral membrane proteins recovery in maintaining sperm viability was also lower than oviductal APM (p<0.01).

EXAMPLE 9

Microencapsulation of Sperm

A gel containing the spermatozoa is formed in an alginate matrix by means of exposure to calcium (divalent ion) and then forming a hydrogel layer of polymer shell, from materials such as poly-1-lysine, polyvinylamine, polyarginine or protamine sulphate.

The content is then changed to a sol by removing the divalent ions with ethylenediaminetetraacetic acid (EDTA)

The invention has been described and illustrated by means of a number of different specific examples. It will be appreciated, however, that the invention is not limited to the disclosure of these examples.

The inventors have described a distinct dose response effect of APM preparations on the maintenance of boar sperm viability.

The present inventors have shown that heat treatment of oviductal APM preparations abolished their biological activity. Proteins unfold or denature under various conditions; thermal energy from heat can break the weak bonds, destabilising protein native conformation and causing loss of biological activity. The inventors have therefore shown that proteins in these membrane fractions as the active factor(s) responsible for oviductal APM biological activity.

The present inventors have identified that biological activity is still present in the peripheral membrane fraction. Therefore, the inventors have shown that active protein(s) responsible for the maintenance of sperm viability by oviductal APM belongs to the peripheral membrane protein category. This finding has physiological significance, and important technical implications regarding future strategies for purification and characterisation of active protein(s) responsible for maintaining boar sperm viability by oviductal APM preparations.

Preparation of the APM fractions involved extensive washing steps. These washing steps did not remove the biological activity. Thus, the inventors have shown that the membrane components responsible for the bioactivity are not readily soluble.

The proteins obtained by preparation of the APM fractions are unlike soluble proteins which are derived from the oviduct. These oviduct proteins are secreted into the oviduct and, if any were present at the start of the preparation of APM to obtain the present invention, these would certainly have been washed away by the washing steps.

The present invention shows that peripheral membrane protein fractions isolated from oviduct epithelial cells, when co-incubated with spermatozoa at 39° C., extend the life of the spermatozoa for 2–3 days beyond the maximum lifespan of control spermatozoa incubated without peripheral membrane protein fractions.

The present invention further identifies a method by which APM fractions of freshly collected porcine oviductal cells can be isolated and tested for activity. Using this method, fractions have been studied extensively, and are shown to retain the ability to prolong the life of spermatozoa at 39° C., beyond the lifespan of control spermatozoa. To confirm that APM fractions from reproductive, rather than any, tissues are required for the prolongation of spermatozoa life, membrane fractions from duodenum, lung and kidney were also tested. These preparations were shown not to be comparable to those from the oviduct.

In conclusion, the present invention has demonstrated the ability of oviductal APM to support and prolong sperm viability in a dose dependent manner. This effect was limited to APM obtained from oviductal tissue. Furthermore it seems the active factor(s) involved in the maintenance of sperm viability by oviductal APM can be categorised as peripheral membrane proteins.

The use of AI has expanded considerably in the UK over the last 10 years, from around 14% in the early 1990's to about 50–60% of breeding at the present time.

Semen can be stored in dilute suspension in commercial diluents for about 3–5 days at ambient temperature. AI centres specialise in the collection of semen; they send it in diluted form by guaranteed next-day mail delivery to farmers, who then perform the AI on-farm using equipment also supplied by the AI centres. The semen can be kept alive on farms for 3–5 days, provided the temperature at which it is stored does not fall below 15° C.

Semen is known to be difficult to freeze; the viability of sperm is greatly reduced following cryopreservation. The present invention provides means for sperm viability to be higher following cryopreservation, thus enabling efficient freezing and subsequent provision of high numbers of viable sperm following freezing.

The present invention provides an effective diluent additive which enables AI centre operators to extend the shelf-life of the diluted semen beyond the 3–5 days currently guaranteed. Further, the present invention enables cryopreservation of the semen without loss of fertility. In addition, the present invention enables increased dilution of the semen without loss of fertility and further the present invention provides a means of increasing fertility.

The present invention thus enables AI centres to reduce the size of their herds, thus reducing the output of waste, a goal that has recently been given high priority by the UK government and the EU.

The invention claimed is:

1. A method of improving and/or prolonging sperm viability which comprises contacting spermatozoa with an isolated, cell-free, salt-extracted, soluble peripheral protein fraction of oviductal apical plasma membrane.

2. The method according to claim 1 in which the spermatozoa are contacted with an isolated, cell-free, salt-extracted, soluble peripheral membrane protein fraction of oviductal apical plasma membrane in vitro.

3. The method according to claim 1 in which the spermatozoa are boar spermatozoa and the peripheral membrane fraction is of porcine oviductal apical plasma membrane.

4. A method of improving and/or prolonging sperm viability following cryopreservation which comprises contacting spermatozoa with an isolated, cell-free, salt-extracted, soluble peripheral membrane protein fraction of oviductal apical plasma membrane.

5. A method of improving and/or prolonging sperm viability during cryopreservation which comprises contacting spermatozoa with an isolated, cell-free, salt-extracted, soluble peripheral membrane protein fraction of oviductal apical plasma membrane.

6. A method of improving and/or prolonging sperm viability during in vitro fertilisation which comprises contacting spermatozoa with an isolated, cell-free, salt-extracted, soluble perpheral membrane protein fraction of oviductal apical plasma membrane.

7. A method for improving and/or prolonging sperm viability which comprises contacting spermatozoa with an isolated, cell-free, salt-extracted, soluble peripheral membrane protein fraction of oviductal apical plasma membrane in which the concentration of the protein fraction is between approximately 0.1 µg/L and approximately 1 g/L.

8. The method according to claim 7 in which the concentration of the protein fraction is between approximately 5 µg/L and approximately 400 µg/L.

9. The method according to claim 7 in which the concentration of the protein fraction is between approximately 25 µg/L and approximately 200 µg/L.

10. A method of improving and/or prolonging semen survival following sex-sorting of the spermatozoa for X- (female) and Y-bearing (male) spermatozoa cells which comprises contacting spermatozoa with an isolated, cell-free, salt-extracted, soluble peripheral protein fraction of oviductal apical plasma membrane.

* * * * *